United States Patent
Kuo et al.

(10) Patent No.: US 6,472,466 B2
(45) Date of Patent: Oct. 29, 2002

(54) MULTIFUNCTIONAL IMINE-ESTERS AS NOVEL CROSSLINKERS FOR SURFACE COATINGS

(75) Inventors: Thauming Kuo, Kinsport, TN (US); Jeffery Earl Grant Powell, Blountville, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 09/887,133

(22) Filed: Jun. 22, 2001

(65) Prior Publication Data

US 2001/0036984 A1 Nov. 1, 2001

Related U.S. Application Data

(62) Division of application No. 09/311,154, filed on May 13, 1999, now abandoned.
(60) Provisional application No. 60/112,402, filed on Dec. 15, 1998.

(51) Int. Cl.$^7$ .............................. C08J 3/00; C08K 3/20; C08L 61/22; C08F 20/00
(52) U.S. Cl. ....................... 524/593; 524/597; 525/437; 525/441
(58) Field of Search ................ 524/593, 597; 525/437, 441

(56) References Cited

U.S. PATENT DOCUMENTS 5,814,689 A  9/1998  Goldstein et al.

OTHER PUBLICATIONS

Tahmassebi, Deborah C. and Sasaki, Tomikazu, "Synthesis of a Three–Helix Bundle Protein by Reductive Amination", *J. Org. Chem.*, 1998, vol. 63, (728–731).

Shono, Tatsuya et al, "A Novel Method of Stereoselective Synthesis of (IR, 2R)–Diarylethylenediamines by Reductive Intramolecular Coupling of Aromatic Diimines", *Tetrahedron Letters*, 1992, vol. 33, (5559–5562).

"Oxidation of Amino Acid Esters into N–Hydroxyamino Acid Derivatives," by T. Polonski and A. Chimiak, Department of Organic Chemistry, Technical University of Gdansky, Poland, Tetrahedron Letters No. 28, pp. 2453–2456, 1974; Pergamon Press.

"1,3–Dipolar Cycloaddition Reactions of Imines of α–Amino–Acid Esters: X–Ray Crystal and Molecular Structure of Methyl 4–(2–Furyl)–2,7–Diphenyl–6,8–Dioxo–3,7–Diazabicyclo[3.3.0]Octane–2=Carboxylate," by Ronald Grigg, James Kemp, George Sheldrick, and Jill Trotter; J.C.S. Chem. Comm., 1978, pp. 109–111.

"Synthesis of a New Trialdehyde Template for Molecular Imprinting," by Deborah C. Tahmassebi and Tomikazu Sasaki; J. Org. Chem., 1994, 59, pp. 679–681.

*Primary Examiner*—Patrick D. Niland
(74) *Attorney, Agent, or Firm*—Bernard J. Graves, Jr.; Rose M. Allen

(57) ABSTRACT

The present invention describes the preparation of multifunctional imine-esters and their application as novel crosslinkers for surface coatings. The imine-esters are prepared by reacting a di- or tri-aldehyde with an α-aminoester such as glycine ethyl ester hydrochloride. These novel crosslinkers may then be formulated with polyesters containing maleic anhydride residues to give enamel coating formulations. The enamels may be cured by a 1,3-dipolar cycloaddition mechanism to give carbon-carbon bonds and cyclic structure. Coatings thus prepared have advantages of low toxicity, no formaldehyde evolution, and improved performance.

2 Claims, No Drawings

MULTIFUNCTIONAL IMINE-ESTERS AS NOVEL CROSSLINKERS FOR SURFACE COATINGS

This is a division of Application Ser. No. 09/311,154, filed May 13, 1999, now ABN and claims benefit of Application Serial No. 60/112,402, filed Dec. 15, 1998.

BACKGROUND OF THE INVENTION

In a thermoset coating system, it is required to have a crosslinking mechanism in order to obtain the desirable film properties such as solvent resistance, weatherability, and mechanical strength. Melamine/formaldehyde and isocyanates are the two common classes of crosslinkers used for polyol resins in the current coating technology. However, there has been extensive research effort in the coating industry to explore alternatives for these two crosslinking systems in order to meet current demands related to safety regulations and coating performance. These demands are resulted from concerns over the toxic nature of the isocyanates and problems associated with the melamine/formaldehyde system such as formaldehyde evolution and poor acid-etch resistance. In the present invention, a new class of crosslinkers have been discovered which may meet such demands.

It has been disclosed in the literature that imines of α-amino acid esters may undergo 1,3-dipolar cycloaddition on heating with dipolarophiles such as maleic anhydride and dimethyl acetylenedicarboxylate to form adducts with cyclic structures. The imines may also be prepared by reacting hydrochloride salts of amino acid esters with benzaldehyde in the presence of triethylamine. The preparation of a tribenzaldehyde by reacting cyanuric chloride with p-hydroxybenzaldehyde has also been disclosed. The prior art, however, does not teach the preparation of multifunctional imine-esters and their application as crosslinkers for thermoset coatings.

BRIEF SUMMARY OF THE INVENTION

The present invention describes the preparation of multifunctional imine-esters and their application as novel crosslinkers for surface coatings. The imine-esters may be formulated with polyesters containing maleic anhydride residues to give enamel formulations. These enamels may be cured by a 1,3-dipolar cycloaddition mechanism to give carbon-carbon bonds and cyclic structure. Coatings thus prepared have advantages of low toxicity, no formaldehyde evolution, and improved performance.

DETAILED DESCRIPTION OF THE INVENTION

In the present invention, it has been discovered that multifunctional imine-esters act as novel crosslinkers for coating applications. The imine-esters may be prepared by reacting a di- or tri-aldehyde with an aminoester such as glycine ethyl ester hydrochloride (GEE). As shown in the reaction schemes below, di(imine-ester) (1) may be prepared by reacting terephthalaldehyde with GEE; whereas, tri(imine-ester) (2) may be prepared by reacting GEE with tribenzaldehyde (3) which in turn was synthesized by reacting cyanuric chloride with p-hydroxybenzaldehyde.

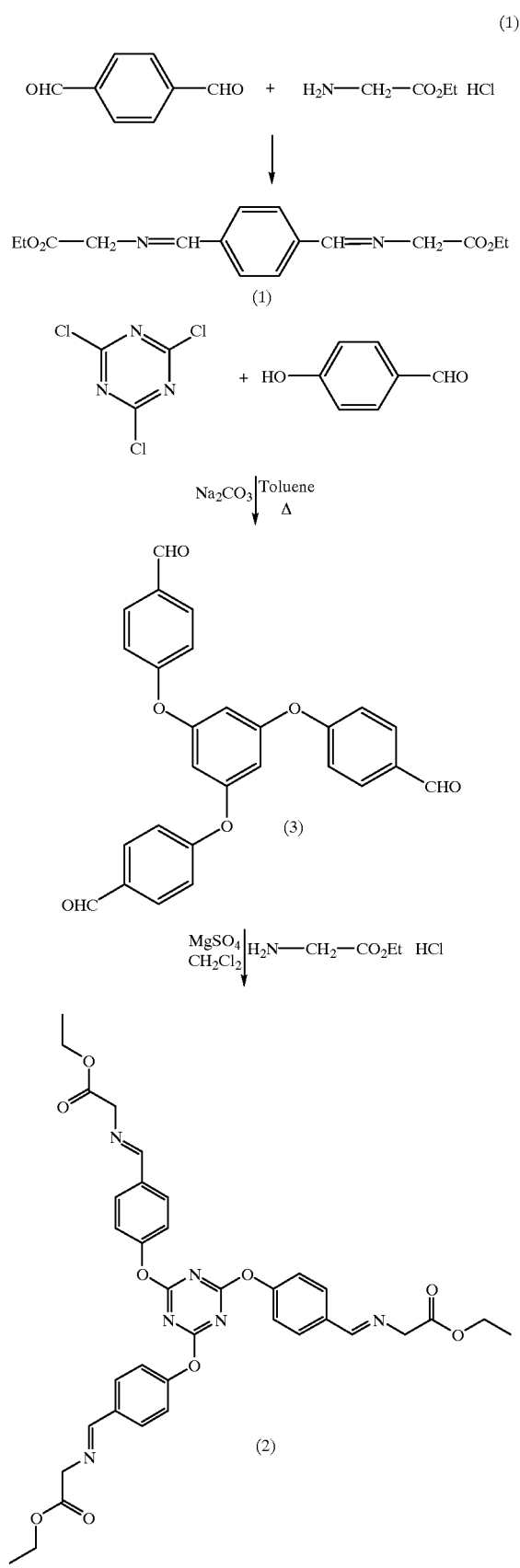

These imine-ester crosslinkers may then undergo 1,3-dipolar cycloaddition on heating with maleic anhydride moieties to give highly desired carbon-carbon bonds and cyclic structure. This novel crosslinking mechanism may be demonstrated by the reaction of di(imine-ester) (1) with dimethyl maleate as illustrated in the reaction scheme below. The di(imine-ester) is first transformed on heating into an azomethine ylid which may then be readily reacted with dimethyl maleate to give a di-substituted adduct with cyclic structure.

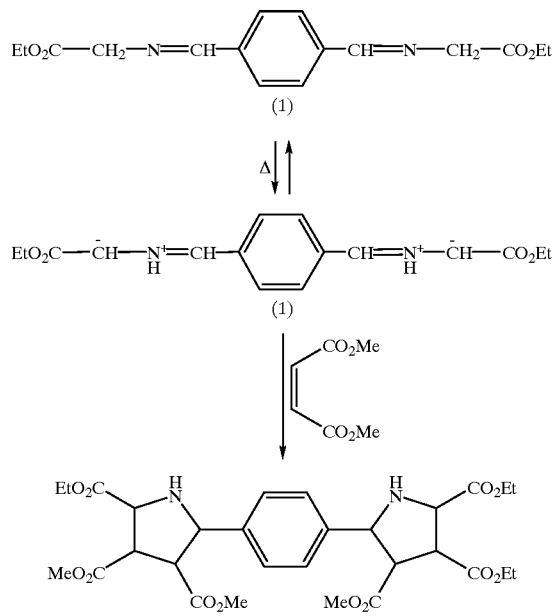

In the present invention, the imine-ester crosslinkers may be formulated with a polyester resin containing maleic anhydride residues to give baking enamels. The enamels thus prepared may then be coated on a substrate and subsequently baked to give cured films. The coatings have been found to be substantially crosslinked as evidenced by the good solvent resistance. The crosslinkers of the present invention have advantages of low toxicity, no formaldehyde evolution, and formation of cyclic structures for improved coating performance.

Thus, in one embodiment of this invention there is provided a crosslinker composition comprising the reaction products of (a) a compound with multifunctional aldehyde groups represented by the formula Z—[R—CHO]$_n$
   wherein Z is a multifunctional residue; R is Ar or alkyl, n is 2 or 3 and (b) an amine with an electron withdrawing group at the α position represented by the formula $H_2N$—CH(R)—E.W.
   wherein R is H or alkyl; E.W. is an electron withdrawing group selected from $CO_2R$, CN, COR, Cl, Br, or I and the like.

The equivalent ratio of (b) to (a) is preferably about 0.8 to 1.5. A more preferred equivalent ratio is about 1.0 to 1.3, and the most preferred equivalent ratio is about 1.0 to 1.1.

In another embodiment of the present invention, there is provided a crosslinker composition comprising the reaction products of (a) a compound with multifunctional α-aminoester groups represented by the formula Z—[OOCCH(R)$NH_2$]$_n$
   wherein Z is diol, triol, or polyol residues and R is H, or alkyl, n is 2 or 3 and (b) an aromatic or aliphatic aldehyde The equivalent ratio of (b) to (a) is preferably about 0.8 to 1.5. A more preferred equivalent ratio is about 1.0 to 1.3, and the most preferred equivalent ratio is about 1.0 to 1.1.

In yet another embodiment of the present invention there is provided an enamel composition, comprising (a) about 50 to 90 weight % of a polyester, based on the total weight of (a) and (b), comprising the reaction products of
   (1) about 40 to 65 mole % of a diol, based on the total moles of (1), (2), (3), and (4),
   (2) about 0 to 20 mole % of a polyol, based on the total moles of (1), (2), (3), and (4),
   (3) about 0 to 25 mole % of a diacid residue, based on the total moles of (1), (2), (3), and (4),
   (4) about 10 to 60 mole % of an ethylenically unsaturated diacid residue, based on the total moles of (1), (2), (3), and (4), (b) about 10 to 50 weight % of an imine-ester crosslinker of the present invention, based on the total weight of (a) and (b); and (c) a sufficient amount of an organic solvent to reduce the enamel viscosity to an applicable level.

A preferred weight % of (a) is about 60 to 50 and (b) is about 20 to 40. A more preferred weight % of (a) is about 60 to 70 and (b) is about 30 to 40.

Preferred mole % of (1) is about 45 to 60, (2) is about 3 to 15, (3) is about 5 to 20, and (4) is about 15 to 50. A more preferred mole % of (1) is about 50 to 55, (2) is about 5 to 10, (3) is about 8 to 15, and (4) is about 20 to 40.

This invention may be further illustrated by the following examples of preferred embodiments thereof, although it will be understood that these examples are included merely for purposes of illustration and are not intended to limit the scope of the invention unless otherwise specifically indicated.

EXAMPLES

Example 1

Preparation of Di(imine-ester) (1)

To a three-neck round-bottom flask equipped with a mechanical stirrer and a nitrogen inlet were charged the following: terephthalaldehyde 17.58 g (0.13 mole), glycine ethyl ester hydrochloride 36.49 g (0.26 mole), magnesium sulfate 21.68 g, triethyl amine 30.42 g, and the solvent, methylene chloride, 320 ml. The mixture was allowed to stir at room temperature for six hours. After the reaction, the solid was removed by suction filtration and the filtrate collected. The filtrate was then extracted repeatedly with saturated NaCl solution and water until the pH was close to 7-8. The organic layer was collected and dried over sodium sulfate. The solvent was then removed under reduced pressure to give 34.78 g of yellow powders.

Example 2

Preparation of Tribenzaldehyde (3)

To a three-neck round-bottom flask equipped with a mechanical stirrer, a water condenser, and a nitrogen inlet were charged the following: cyanuric chloride 18.0 g (0.097 mole), p-hydroxybenzaldehyde 48.0 g (0.393 mole), sodium carbonate 300.0 g, and the solvent, toluene, 1500 ml. The slurry was then stirred, heated slowly to 90° C., and held for four hours. The temperature was then increased to 100° C. and held for about one day. After the reaction, the solid was removed by suction filtration and washed with hot ethyl acetate twice. The filtrate was then extracted repeatedly with 10% sodium carbonate and water. The organic layer was collected and dried over sodium sulfate. The solvent was then removed under reduced pressure and the resulting residue recrystallized from ethyl acetate to give 24.1 g of white powders.

Example 3

Preparation of Tri(imine-ester) (2)

To a three-neck round-bottom flask equipped with a mechanical stirrer and a nitrogen inlet were charged the following: tribenzaldehyde (3) 10.0 g (0.022 mole), glycine ethyl ester hydrochloride 11.4 g (0.082 mole), magnesium sulfate 9.5 g, triethyl amine 9.1 g, and the solvent, methylene chloride, 137.5 ml. The mixture was allowed to stir at room temperature for 24 hours. After the reaction, the solid was removed by suction filtration and the filtrate collected. The filtrate was then extracted repeatedly with saturated NaCl solution and 20% $NH_4Cl$ until the pH was close to 7-8. The organic layer was collected and dried over sodium sulfate. The solvent was then removed under reduced pressure to give 15.78 g of yellowish, viscous product.

Example 4

Preparation of Polyester Resin Containing Maleic Anhydride Residues

To a three-neck, round-bottom flask equipped with a mechanical stirrer, a steam-jacked partial condenser, a Dean-Stark trap, a nitrogen inlet, and a water condenser were charged neopentyl glycol (NPG), 267.83 g (2.58 mole); trimethylolpropane (TMP), 34.50 g (0.26 mole); isophthalic acid (IPA), 81.80 (0.49 mole); maleic anhydride, 144.93 g (1.48 mole); and Fascat 4100 catalyst (Atochem North America), 0.46 g. The mixture was heated and held for one hour at 160° C. The condensate (water) was collected in the Dean-Stark trap. The reaction was allowed to continue at 180° C. for one hour and at 200° C. for about two hours until an acid number of 1.3 mg KOH/g was obtained. The resulting resin was allowed to cool to 125° C. and xylene 120.30 g added. The final resin had 80% solids.

Example 5

Coating Formulation and Testing

Enamel 1: An enamel formulation was prepared by mixing di(imine-ester) (1) 2.50 g from Example 1, polyester resin 3.12 g from Example 4, a flow control additive, FC-430 (3M Co.), 0.06 g, and a solvent blend of methyl amyl ketone (70 wt. %), xylene (15 wt. %), and ethyl 3-ethoxypropionate (15 wt. %) 2.65 g. The enamel was then coated on a cold-rolled steel test panel and baked at 150° C. for 30 min. The resulting cured coating was then tested and found to have the following properties: MEK double rubs, 200; gloss 60°/20°=99/96; pencil hardness 2H; impact resistance, forward/reverse =30/10.

Enamel 2: An enamel formulation was prepared by mixing tri(imine-ester) (2) 2.00 g from Example 3, polyester resin 3.75 g from Example 4, a flow control additive, FC430, 0.06 g, and xylene 2.52 g. The enamel was then coated on a cold-rolled steel test panel and baked at 150° C. for 30 min.

The resulting cured coating was then tested and found to have the following properties: MEK double rubs, 191; gloss 60°/20°=99/98; pencil hardness 2H; impact resistance, forward/reverse=20/<10.

The invention has been described in detail with particular reference to preferred embodiments thereof, but it will be understood that variations and modifications may be effected within the spirit and scope of the invention.

What is claimed is:

1. An enamel composition comprising:
   (a) about 50 to 90 weight % of a polyester, based on the total weight of (a) and (b), comprising the reaction products of
      (1) about 40 to 65 mole % of a diol, based on the total moles of (1), (2), (3), and (4),
      (2) about 0 to 20 mole % of a polyol, based on the total moles of (1), (2), (3), and (4),
      (3) about 0 to 25 mole % of a diacid residue, based on the total moles of (1), (2), (3), and (4),
      (4) about 10 to 60 mole % of an ethylenically unsaturated diacid residue, based on the total moles of (1), (2), (3), and (4),
   (b) about 10 to 50 weight % based on the total weight of (a) and (b), of an imine-ester crosslinker composition comprising the reaction products of
      (1) a compound with multifunctional aldehyde groups represented by the formula:

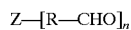

wherein Z is a multifunctional residue; R is Ar or alkyl; n is 2 or 3; and
      (2) an amine with an electron withdrawing group at the α position represented by the formula:

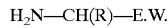

wherein R is H or alkyl; E.W. is an electron withdrawing group selected from $CO_2R$, CN, COR, Cl, Br, or I; and
   (c) an organic solvent.

2. An enamel composition comprising:
   (a) about 50 to 90 weight % of a polyester, based on the total weight of (a) and (b), comprising the reaction products of
      (1) about 40 to 65 mole % of a diol, based on the total moles of (1), (2), (3), and (4),
      (2) about 0 to 20 mole % of a polyol, based on the total moles of (1), (2), (3), and (4),
      (3) about 0 to 25 mole % of a diacid residue, based on the total moles of (1), (2), (3), and (4),
      (4) about 10 to 60 mole % of an ethylenically unsaturated diacid residue, based on the total moles of (1), (2), (3), and (4),
   (b) about 10 to 50 weight % based on the total weight of (a) and (b), of an imine-ester crosslinker composition comprising the reaction products of
      (1) a compound with multifunctional α-aminoester groups represented by the formula:

wherein Z is diol, triol, or polyol residues and R is H, or alkyl; n is 2 or 3; and
      (2) an aromatic or aliphatic aldehyde; and
   (c) an organic solvent.

* * * * *